United States Patent [19]

Brown

[11] Patent Number: 4,676,274

[45] Date of Patent: Jun. 30, 1987

[54] CAPILLARY FLOW CONTROL

[76] Inventor: James F. Brown, 6500 Hanover Heights Trail, Clifton, Va. 22024

[21] Appl. No.: 706,728

[22] Filed: Feb. 28, 1985

[51] Int. Cl.[4] ............................................. F15B 21/00
[52] U.S. Cl. ..................................... 137/806; 137/252; 422/82; 422/103
[58] Field of Search ...................... 137/806, 251.1, 252; 422/58, 100, 101, 103

[56] References Cited

U.S. PATENT DOCUMENTS

| 2,654,387 | 10/1953 | Innes | 137/251.1 |
| 2,834,366 | 5/1958 | Bond, Jr. | 137/251.1 |
| 3,111,959 | 11/1963 | Allen et al. | 137/251.1 |
| 3,327,728 | 6/1967 | Huling | 137/252 |
| 3,357,233 | 12/1967 | Roof | 137/806 |
| 3,481,205 | 12/1969 | Schmidlin | 137/251.1 |
| 4,254,083 | 3/1981 | Columbus | 422/58 |
| 4,271,119 | 6/1981 | Columbus | 422/50 |
| 4,399,102 | 8/1983 | Karlberg et al. | 422/82 |
| 4,426,451 | 1/1984 | Columbus | 422/58 |

*Primary Examiner*—A. Michael Chambers
*Attorney, Agent, or Firm*—John P. Snyder

[57] ABSTRACT

Capillary flow of a principal fluid is controlled through the medium of a control fluid. The two fluids are capable of forming fluid/fluid interfaces therebetween in which the potential energy states of the two fluids on either side of the interface are different. Flow control of the principal fluid is effected by changing the kind of fluid/fluid interface by reversing the potential energy states of the two fluids at the interface or interfaces therebetween.

11 Claims, 22 Drawing Figures

FIG. 1
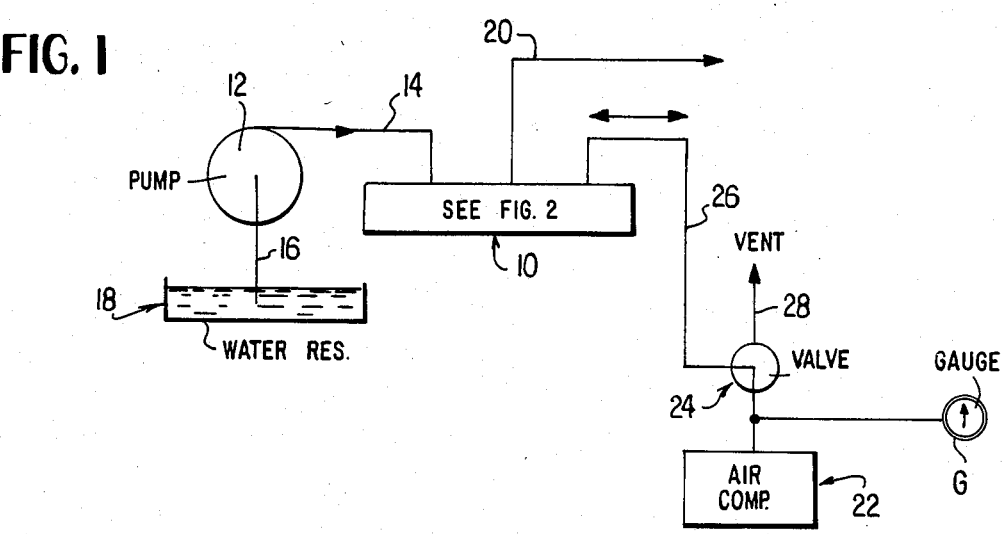
FIG. 2
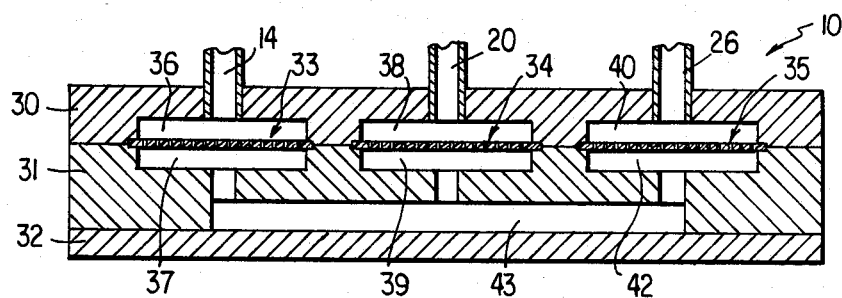
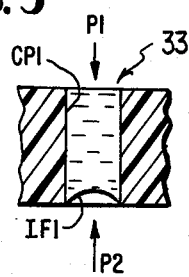
FIG. 3
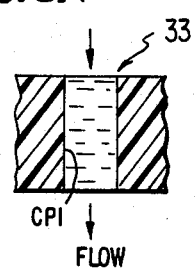
FIG. 3A
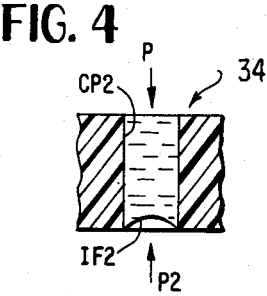
FIG. 4
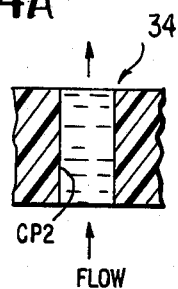
FIG. 4A
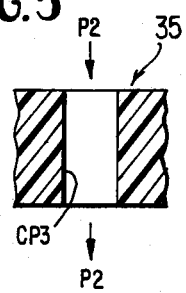
FIG. 5
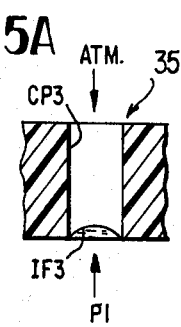
FIG. 5A

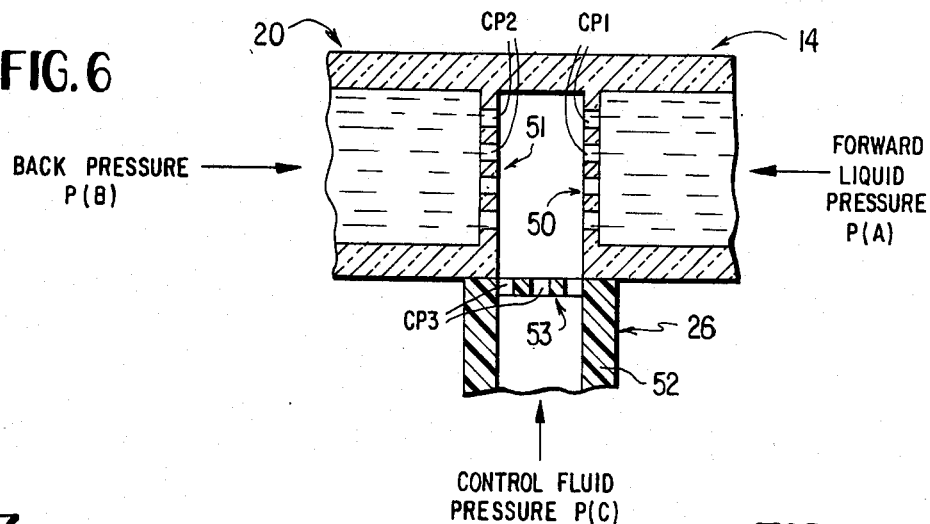
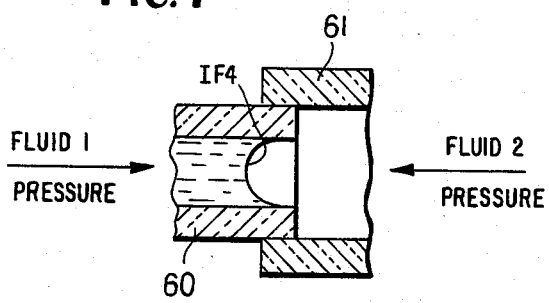
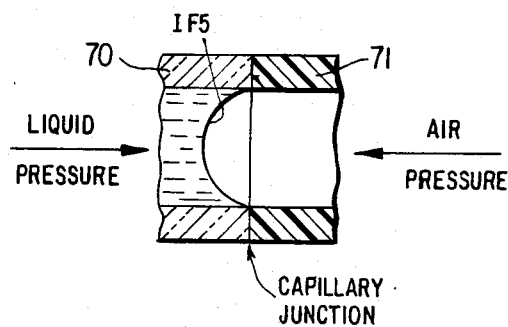
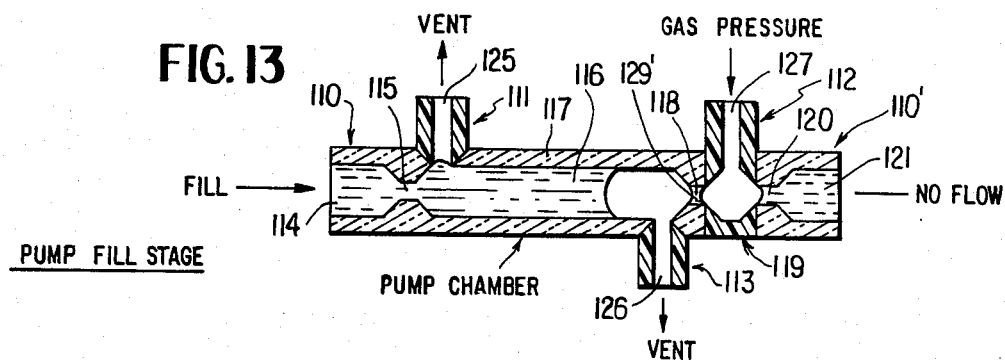
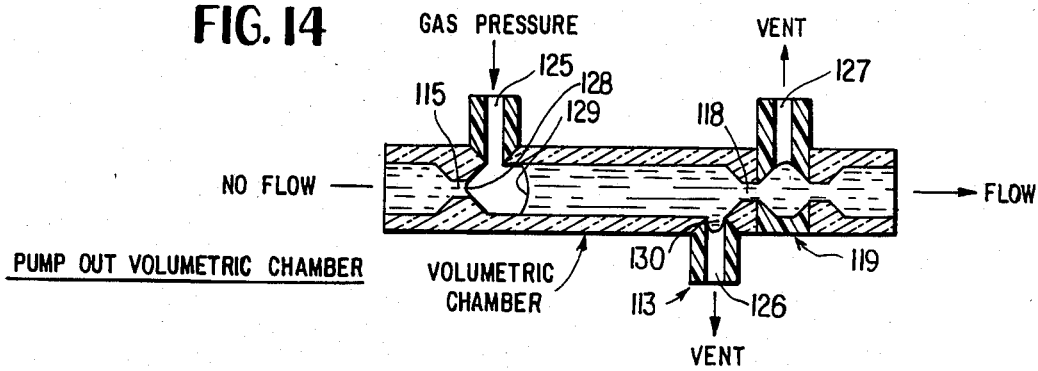

CAPILLARY FLOW CONTROL

BACKGROUND & BRIEF SUMMARY OF THE INVENTION

Prior Art

The closest prior art of which applicant is aware is as follows:
U.S. Pat. No. 3,607,083; Thiers; Sept. 21, 1971
U.S. Pat. No. 4,233,029; Nov. 11, 1980
U.S. Pat. No. 4,254,083; Columbus; Mar. 3, 1981
U.S. Pat. No. 4,264,560; Natelson; Apr. 28, 1981
U.S. Pat. No. 4,271,119; Columbus; June 2, 1981
U.S. Pat. No. 4,310,399; Columbus; Jan. 12, 1982
U.S. Pat. No. 4,399,102; Karlberg; Aug. 16, 1983
U.S. Pat. No. 4,426,451; Columbus; Jan. 17, 1984

Although the above patents involve fluid flow systems which may utilize capillary flow principles, the basic concept of shifting a control fluid/principal fluid interface for the purpose of influencing or controlling principal fluid flow is not present therein.

Technical Field of Invention

The invention is concerned with principal fluid flow control within a capillary system, in which the flow control is effected by change in the kind of fluid/fluid interface between the principal fluid and a control fluid. The principal fluid and the control fluids have different surface energy levels so as to be capable of providing a fluid/fluid interface therebetween. The change in the kind of fluid/fluid interface, to effect flow control of the principal fluid, is effected by reversing the potential energy states of the principal and control fluids at the locations where the fluid/fluid interfaces are formed, the potential energy states being determined by the surface energy level of the principal fluid or control fluid each in combination with the surface energy level of the material with which it is contact at the location of the interface in question.

More particularly, it relates to fluid flow control systems and is concerned primarily with controlling capillary flow of one fluid (hereinafter the principal fluid) through the intermediary of pressure exerted on a second fluid (hereinafter the control fluid), the principal and control fluids having different surface energy levels and being capable of forming fluid/fluid interfaces therebetween, and wherein the principal fluid normally flows through capillary surface means with which it in combination presents a different potential energy state than does the control fluid in combination with that same surface. Likewise, the control fluid normally is in contact with capillary surface means with which it incombination presents a different potential energy state than does the principal fluid in combination with such surface.

The flow control of this invention is effected by shifting or moving one or more fluid/fluid interfaces from one location, junction or border in which the interface or interfaces are confined within capillary surface means associated with the control fluid to another location or locations in which the fluid/fluid interface or interfaces intrude into or are confined to be within the capillary surface means associated with the principal fluid.

The location or locations of an interface or interfaces, as the case may be, is effected by pressure control of the control fluid, specifically by variation of pressure operating upon the control fluid in such sense as to compel a change of location of the interfaces. At some lower pressure acting on the control fluid, the interface or interfaces will be located at a position which permits full flow of the principal fluid and at some higher pressure on the control fluid, the interface or interfaces will be located to intrude into or to block the capillary means containing the principal fluid thereby respectively to impede or to block the flow of principal fluid.

Prior to the intrusion of the control fluid into the capillary means containing the principal fluid, a fluid/fluid interface will be present at a location within the capillary means for the control fluid which does not materially impede the flow of the principal fluid. It is the intrusion of the control fluid into the capillary means containing the principal fluid which causes a change in location or locations of one or more fluid/fluid interfaces so that it or they are shifted to be within the confines of the capillary means containing the principal fluid thereby to impede or to block the flow of the principal fluid.

It is a particular feature of this invention that the difference in pressure which must be exerted on the control fluid to effect the aforesaid shift in locations of the interfaces is relatively wide and is not of critical nature. The control fluid may for example have a very low pressure (e.g., atmospheric) acting on it when an interface is in non-impeding location or locations. Although the pressure acting on the control fluid when an interface is in impeding or blocking location or locations must be increased to be greater than the pressure acting on the principle fluid, its value may vary over a wide range or "bandwidth" as used herein. Therefore, it is not difficult to select a value of pressure which will effect the requisite shift of interface location.

More particularly, where an impeding or blocking fluid/fluid interface is formed, the principal fluid operating in conjunction with the surface of the flow passage with which it is in contact at one side of the interface represents a different potential energy state than does the control fluid operating in conjunction with the surface area of the flow passage with which it is in contact on the other side of the interface. This factor is important to the bandwidth characteristic referenced above.

According to another aspect of this invention, where the fluid/fluid interfaces are formed, the aforesaid capillary surfaces with which the two fluids are in contact are themselves of different surface energy levels. For example, for a principal fluid having a higher surface energy level than the control fluid and operating in combination with a capillary surface means whose surface energy level is also high, such combination of principal fluid and high surface energy level capillary means presents a lower potential energy state than does the combination of the control fluid and such high surface energy level capillary surface means, whereas the opposite is the case when the principal fluid and the control fluid are in contact with the lower surface energy level capillary surface means within which the control fluid normally operates. Thus, it will be appreciated that such an arrangement is conducive to the bandwidth feature noted above. That is to say, for example, an interface which is concave into the low surface energy capillary means will occur when the interface is in non-impeding or non-blocking location and a concave interface into the high surface energy capillary means will occur when the interface is in impeding or blocking location.

More specifically, the invention is concerned with the capability of controllably establishing one or more pressure stabilized fluid/fluid interfaces between the principal fluid and the control fluid at at least two or more locations within the flow passage means in order to achieve a desired control function. To this end, the invention contemplates the provision of at least two fluid/fluid interface locations within the flow passage for the principal fluid, which locations are defined between different surface energy level portions of the flow passage, each such location or junction defining a border between these different surface energy level portions which allows a control fluid to be introduced into the capillary flow passage means so as to form a principal fluid/control fluid interface stabilized by and at such border, the control fluid serving either to restrict the flow of the principal fluid or to block flow of the principal fluid. In the former instance, the arrangement operates as a flow rate restrictor and in the second instance, as a control valve which, itself, permits other and different devices to be constructed.

The invention contemplates that the interface may be stabilized at the location or junction between a capillary passage and another capillary passage of substantially the same diameter, the materials defining the two surfaces being of different surface energy levels and defining the border; that the interface may be stabilized at the location or junction between a capillary passage and a passage of substantially larger diameter, in which case the smaller capillary passage itself defines the location, junction or border which stabilizes the interface; and that the interface may be stabilized at the junction between two surfaces of different energy levels, which two surfaces are those defining two capillary passages which may be of disparate diameters.

According to the present invention, plural locations, borders or junctions as described above may be used at spaced positions within the flow passage for the principal fluid initially to trap or isolate a predetermined or known volume of the principal fluid and thereafter to release this isolated volume of principal fluid for further controlled flow thereof. This technique may be employed, for example, to meter or to pump or displace known quantities of the principal fluid.

In a particular embodiment of the invention, a device relates to capillary flow control and in particular to controlling such flow with respect to extermely small volumes of a principal fluid. By extremely small volumes of principal fluid, as used herein, is meant volumes which may be as small as in the order of one picoliter.

Although not necessarily restricted thereto, the embodiments of the present invention as are disclosed hereinafter are principally concerned with a liquid/gas system in which either the liquid or the gas may operate as the principal fluid while the other operates as the control fluid.

According to the present invention, a representative liquid/gas system comprises a capillary flow passage means whose capillary surface is formed by a high surface energy level material such as glass whereas the low surface energy surface area is formed by material such as Teflon and wherein the high surface energy level fluid is water and the low surface energy level fluid is air. In this system, either the water or the air may be the principal fluid.

Systems of the present invention may employ porous membranes which function as the capillary flow passage means, in which case the junction is located at one end of the capillary passage means which are defined by the membrane.

The applications of the present invention are many and varied and although a few examples of particular applications are specified hereinafter, the invention is by no means limited thereto.

BRIEF DESCRIPTION OF THE DRAWING FIGURES

FIG. 1 is a diagrammatic view of a fluid flow system employing the principles of this invention;

FIG. 2 is an enlarged section of the capillary flow control unit of FIG. 1;

FIGS. 3, 3A, 4, 4A, 5 and 5A are enlarged views of single capillary passages of FIG. 2 illustrating the locations and details of the fluid/fluid interfaces during flow and non-flow conditions;

FIG. 6 is an enlarged section illustrating one form of a valve in accord with this invention;

FIG. 7 is an enlarged view illustrating one form of capillary junction illustrative of the invention;

FIG. 8 is an enlarged view illustrating another form of capillary junction;

FIG. 13 is an enlarged section illustrating a metering device in accord with the invention;

FIG. 14 illustrates the device in FIG. 13 during transfer of the metered fluid;

DETAILED DESCRIPTION OF THE INVENTION

Figure 9:
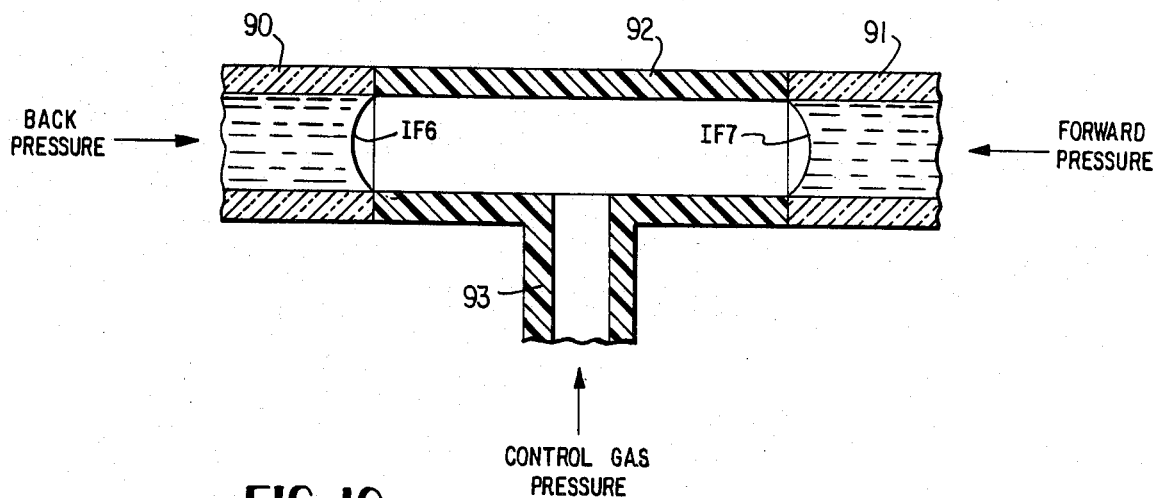
FIG. 9 is an enlarged view of a preferred type of configuration for a valve.

FIG. 1 illustrates an embodiment of the present invention utilizing the flow control principles specified herein. This system is intended for macro flow control, that is, it is intended to operate to control relatively large flows as opposed to micro flow control where, for example, the flow may be restricted to be within a very small capillary system as might be embodied in a microscope slide for individual cell manipulation.

As illustrated, the system shown includes the valve mechanism indicated generally by the reference character 10 and shown in more detail in FIG. 2 in association with a variable pressure pump 12 which pumps water under pressure in the discharge line 14, the pick-up being through the inlet conduit extending to the water reservoir indicated generally by the reference character 18. Thus, in this case, water is the principal fluid and its flow is controlled by the valve 10 by air acting as the control fluid so that at the discharge flow passage conduit 20, there is a flow or no flow condition dependent upon the condition of the valve 10 which will be described with greater particularity hereinbelow. The system also includes a variable pressure air compressor 22 discharging through a manually controlled valve 24 to the air line 26 connected with the valve 10. The manually controlled valve 24 is positionable so that either the pressure provided by the compressor 22 is present in the line 26 or the line 26 is vented to atmosphere as indicated by the vent passage 28. The gauge G measures the pressure in the line 26 when the air compressor 22 is connected thereto through the valve 24.

The valve 10 shown in FIG. 2 is constructed in accord with the principles of this invention. To this end, the three polymethylmethacrylate plates 30, 31 and 32 are constructed and arranged so that when layered together as shown in FIG. 2, the three porous membranes 33, 34 and 35 are held in position as shown. The membrane 33 is provided with a chamber 36 above it and a chamber 37 below it. Similarly, the membrane 34 is provided with a chamber 38 above it and a chamber 39 below it and, lastly, the membrane 35 is likewise provided with a chamber 40 above it and a chamber 41 below it. The three chambers 36, 38 and 40 are in communication respectively with the lines 14, 20 and 26 and it will be seen that the three chamber 37, 39 and 42 are in communication with the common chamber 43 substantially as is shown.

As will be appreciated, the system shown in FIG. 2 is a water/air system. FIGS. 3 and 3A are somewhat idealized illustrations depicting a single one of the capillary passages through the porous membrane 33. Likewise, FIGS. 4 and 4A are idealized and illustrate a single one of the capillary passages through the porous membrane 34 and, lastly, FIGS. 5 and 5A show idealized representations of a single one of the capillary passages through the porous membrane 35.

FIGS. 3, 4 and 5 illustrate the conditions at the capillaries of the several membranes 33, 34 and 35 when the valve 10 is in the shut-off condition. The porous membranes 33 and 34 are made of Nylon and are wettable by the principal fluid, in this instance, water. The membrane 35, however is made of Teflon and is non-wettable by the principal fluid water. Thus, when the line 26 is pressurized, at the pressure P2, the air will initially flow through the porous membrane 35 from the chamber 40 to the chamber 52 and thence to the chamber 43 to displace water therefrom which is forced to pass through the two membranes 33 and 34 until the conditions of FIGS. 3 and 4 are obtained. As shown in FIG. 3, the water pressure P1 supplied by the pump 12 over the line 14 and filling the chamber 36 is opposed at one end of the capillary passage CT1 so that the air in the chamber 37 below the membrane 33 forms a meniscus at the lower end of the capillary passage CP1 as is illustrated in FIG. 3 and which meniscus defines the water/air interface IF1 as illustrated. It can be shown that if the pressure P2 slightly exceeds the pressure P1, the interface IF1 is stabilized and will be located at the lower end of the capillary passage CP1 as is illustrated in FIG. 3 and correspondingly, the flow of water through the line 14, through the membrane 33 and into the chamber 43 and thence upwardly through the membrane 34 to the line 20 will be terminated. At the same time, as is illustrated in FIG. 4, the water pressure head P operating in opposition to the air pressure P2 in the chamber 39 will form a further water/air interface IF2 as is illustrated, thus preventing escape of air from the chamber 43 and 39 through the porous membrane 34. In this condition of the valve, the capillary passage CP3 through the membrane 35 will pass the air under the pressure P2 substantially as is shown, it being appreciated that the porous membrane 35 is made of Teflon which is non-wettable by the principal fluid water.

When the manual valve 24 is vented to atmosphere and the line 26 therefore is at atmospheric pressure, the conditions of FIGS. 3A, 4A and 5A prevail and flow of the principal fluid will pass from the inlet line 14, through the valve 10 and out the discharge line 20. As shown in FIGS. 3A and 4A, water will flow first from the chamber 36 and through the capillary passage CP1 into the chamber 37 and thence into the chamber 43 and into the chamber 39 where it will pass through the capillary passage CP2 and thence into the chamber 38 and out the outlet line 20. At the same time, backflow of water from the chamber 42 to the chamber 40 and the vented air line 26 is prevented by virtue of the Teflon membrane 35 as is illustrated in FIG. 5A, the capillary passage CP3, as is illustrated in FIG. 5A, allowing the atmospheric pressure in the chamber 40 to oppose the water pressure P1 in the chamber 42 to form a water meniscus within the capillary passage CP3 which defines the interface IF3 substantially as is shown.

The Table below illustrates data gathered in operation of the system of FIG. 1. The pump 12 is an FMI Lab Pump, serial no. 4p918, rated at a maximum flow of 3 ML/MIN at 60 PSI and was obtained from Fluid Metering, Inc., Oyster Bay, N.Y. The compressor 22 is of standard design capable of providing air pressure at various ratings from 0 to 80 PSI. In the Table below, the settings of the water pump produce the flow rates as indicated.

TABLE 1

| Water Pump System Setting (0–9) | Control Gas Pressure (PSI) | Observation of |
|---|---|---|
| 2 ML/MIN | Vented to ATM | Water Flow of 0.8 |
| 2 | 20–80 | Flow Stopped |
| 4 ML/MIN | Vented to ATM | Water Flow of 1.4 |
| 4 | 30–80 | Flow Stopped |
| 6 ML/MIN | Vented to ATM | Water Flow of 2 |
| 6 | 40–80 | Flow Stopped |
| 8 ML/MIN | Vented to ATM | Water Flow of 2.5 |
| 8 | 55–80 | Flow Stopped |

The above table illustrates the bandwidth feature of this invention. In each case of controlled flow, the pressure required to terminate flow could be varied over a wide range without causing the blocking flow interfaces to lose stability. The upper value of 80 psi in each case was dictated by the maximum pressure acquired by the air compressor, but even at a flow rate near the maximum, a pressure range of 25 psi was still available for control.

FIGS. 1–5A illustrate the basic principles of the present invention wherein fluid flow control is obtained by controlling capillary flow of the principal fluid through the intermediary of the control fluid, the principal and control fluids having different surface energy levels and being capable of forming a fluid/fluid interface therebetween. In the embodiment shown in FIGS. 1–5A, not only does the water have a higher surface energy level than does the air, but the water operating in conjunction with the Nylon membrane 33 and 34 which are wettable by the water cooperate in combination therewith to provide a lower potential energy state for that combination than for the combination of the Nylon with air.

Similarly, for the Teflon membrane 35, its potential energy state in combination with air is lower than that of the water in combination with the Teflon. Thus, the stable menisci and corresponding fluid/fluid interfaces IF1, IF2 and IF3 are defined, substantially as is described and shown.

A modified form of the control valve shown in FIG. 2 is illustrated in FIG. 6 which, as is the case with the FIG. 2 system is adapted to handle relatively large flow rates of the principal fluids. In this case, the three lines 14, 20 and 26 form a Tee with the materials of the tubes 14 and 20 being formed of glass and being provided with porous glass windows 50 and 51 which correspond respectively with the membranes 33 and 34 by providing a plurality of capillary passages CP1 and a plurality of capillary passages CP2, as is shown. The conduit 26 is formed of Teflon material 52 and is provided with a Teflon window indicated generally by the reference character 53 which corresponds to the Teflon membrane 35 to provide the plurality of capillary passages CP3. As is the case with FIG. 2, the FIG. 6 construction shows a fluid control system in which water is the principal fluid and air is the control fluid and shut-off is obtained as depicted in FIG. 6.

FIGS. 1-6 illustrate one kind of junction which is capable of defining a border at which a fluid/fluid interface is stabilized. This is further illustrated in FIG. 7 wherein the capillary tube 60 is joined with the capillary tube 61. Both of these capillary tubes are shown as formed of high energy material such as glass and the fluid 1 or principal fluid is water whereas the fluid 2 or control fluid may be air or another gas, i.e., it is a fluid whose surface energy level is different from (lower than) the surface energy level of water. The junction at which the interface IF4 is stabilized is defined at the mouth of the capillary passage means defined by the capillary 60 because of the abrupt opening thereof into the much larger passage defined by the capillary 61. The capillary passage defined by the tube 60 is of 10 microns and the inside diameter of the tube 61 is of 20 microns in the particular situation shown. The capillary surfaces are more wettable by the water than by the gas and for this reason little or no principal fluid pressure is required to displace the control fluid from the larger capillary 61. However, control fluid 2 pressure is required to displace the principal fluid 1 from either capillary, this fluid 2 pressure being inversely related to the capillary radius. For the two fluid system such as water and air in the capillaries as described above made of glass, the transition pressure at the junction of the two capillaries is about 6.0 PSI. That is to say, the control fluid pressure must exceed the principal fluid pressure by about 6.0 PSI in order to form the stabilized fluid/fluid interface IF4 illustrated. If the materials of the two capillaries 60 and 61 are such as to be non-wettable by the principal fluid, i.e., made of low surface energy material such as Teflon, similar transition pressures as expressed above obtain but with opposite polarity because the fluids 1 and 2 exchange surface energy properties. Stated otherwise, the interface IF4 would be convcave into the confines of the capillary 61 but would still be stabilized at the junction defined at the mouth of the capillary 60. The reason for the reversal of direction of the interface is that the potential energy state for the combination of the high surface energy level fluid (water) and the now low surface energy level capillary surface (Teflon) provides a higher potential energy state than does the low surface energy level fluid (air) in combination with the low surface energy level Teflon, rather than the reverse for the case when the glass is present.

It will be appreciated that the junction illustrated in FIG. 7 is akin to the plurality of junctions achieved in FIGS. 1-6 at each of the capillary passages illustrated. That is to say, the junction is such as to define a border at the downstream end of the principal flow path defined by the capillary means with which it is associated whereat the interface is formed and stabilized.

A further type of junction is shown in FIG. 8 wherein the glass capillary tube 70 abuts and adjoins the Teflon capillary tube 71, the capillary passages being of substantially the same internal diameter as is shown. In this case, the junction is defined between two materials of different surface energy levels to provide a border at which the interface IF5 is formed and stabilized. In the case of FIG. 8, the presence of the capillary 71 providing a capillary surface of lower surface energy, even though it is of the same diameter as the capillary 70, operates to produce the same effect as the abrupt change in diameter in FIG. 7. The high surface energy level fluid (water) operates in combination with the high surface energy level capillary surface (glass) to provide a lower potential energy state than the potential energy state of the low surface energy level fluid (air) in combination with the high surface energy level capillary surface afforded by the glass at the capillary junction. Therefore, the interface IF5 is concave into the capillary 70, as shown and the border defined at the junction is, as is also the case in FIG. 7, sharply and well defined.

Figure 10:
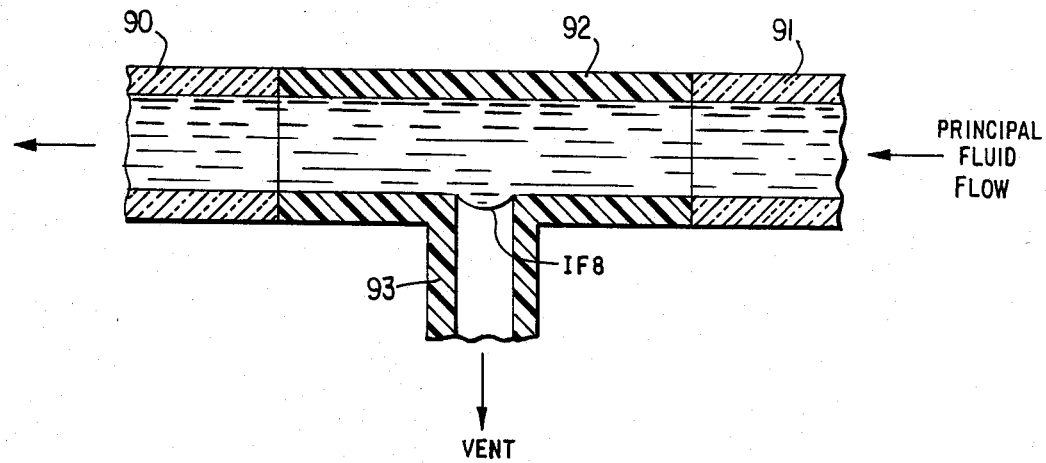
FIG. 10 is identical to FIG. 9 but showing the valve in open condition.

FIGS. 9 and 10 show a control valve construction which is functionally equivalent to those shown in FIGS. 1-6, although, the principal fluid flow rate in this case is extremely small because all of the passages illustrated in FIGS. 9 and 10 are of capillary size. As shown in FIG. 9, there are two capillary glass tubes indicated by the reference characters 90 and 91 and joining them is a Teflon capillary tube 92 having a Tee capillary stem 93 joined thereto substantially as is shown. There are three possible locations for stabilized interfaces in this configuration, two which are indicated at IF6 and IF7 in FIG. 9 and the other of which is at IF8 as in FIG. 10. The flow blocking condition is shown in FIG. 9 wherein the control fluid pressure stabilizes the two interfaces IF6 and IF7 at the locations defined at the borders provided at the capillary junctions formed where the disparate surface energy level materials 90, 92 and 91, 92 join. The flow condition is illustrated in FIG. 10 where the control fluid pressure is vented so that the interface IF8 is now located or formed at the border defined at the junction between the Tee stem 93 and the main body portion 92. It should be noted that this junction at which the interface IF8 is located in FIG. 10 is akin to the type of junction illustrated in FIG. 7.

Figure 11:
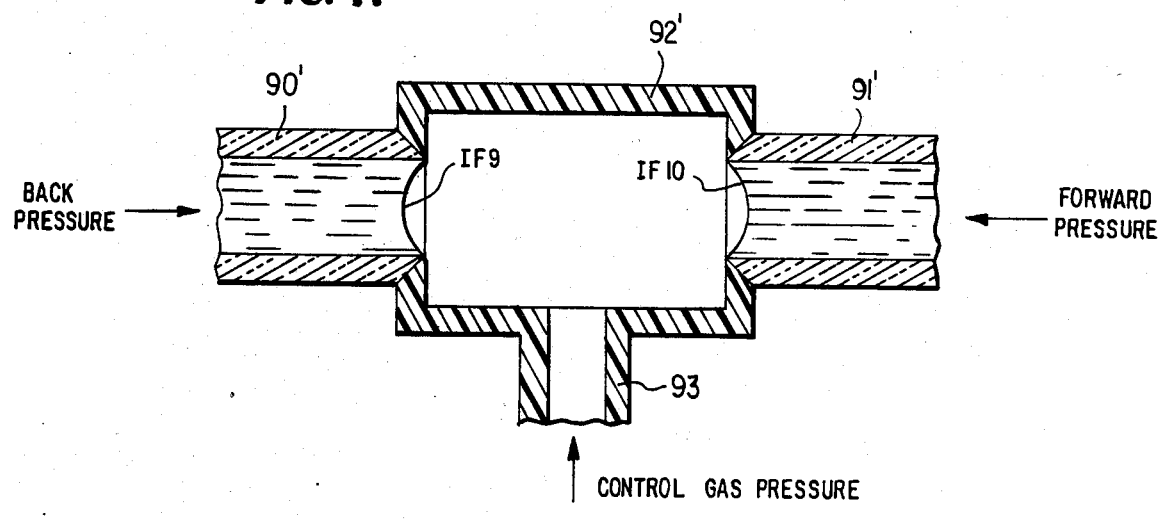
FIG. 11 is a view illustrating another form which the valve may take.

FIG. 11 is substantially identical to FIGS. 9 and 10 but, in this case, the Teflon capillary 92' is of larger internal diameter to provide a junction situation at which the interfaces IF9 and IF10 are located which is more in conformity with the description according to FIG. 7. The border defined at the junction provided at the mouth of the Tee stem 93 and whereat an interface is located in the flow condition of the valve is identical to the situation for the interface IF8 in FIG. 10. The advantage of this construction is that the control gas pressure has a wider "bandwidth" as was previously described, i.e., its pressure is not required to be so precisely controlled in order to form and obtain the stabilized interfaces IF9 and IF10 as would be the case if the capillary tube 90', 91' and 92' were of the same internal diameter as in FIGS. 9 and 10. It will be appreciated that the junction at which the interfaces IF9 and IF10 are formed and stabilized are more akin to those described in conjunction with FIGS. 1-6, i.e., at those ends of the capillary tubes 90' and 91' where they contact the space within the capillary tube 92' containing the control fluid. Consequently, the bandwidth feature as is demonstrated in Table 1 above obtains. It should be noted that there are various ways in which to achieve this bandwidth feature in microflow systems such as is illustrated in FIGS. 9 and 10. For example, aside from the use of an enlarged diameter capillary 92', an arrangement as in FIGS. 9 and 10 may be used but with narrowing or restrictions at the various junctions, see particularly FIGS. 13 and 14 for such an arrangement. Obviously a combination of such arrangements may be employed, see for example FIG. 12.

Figure 12:
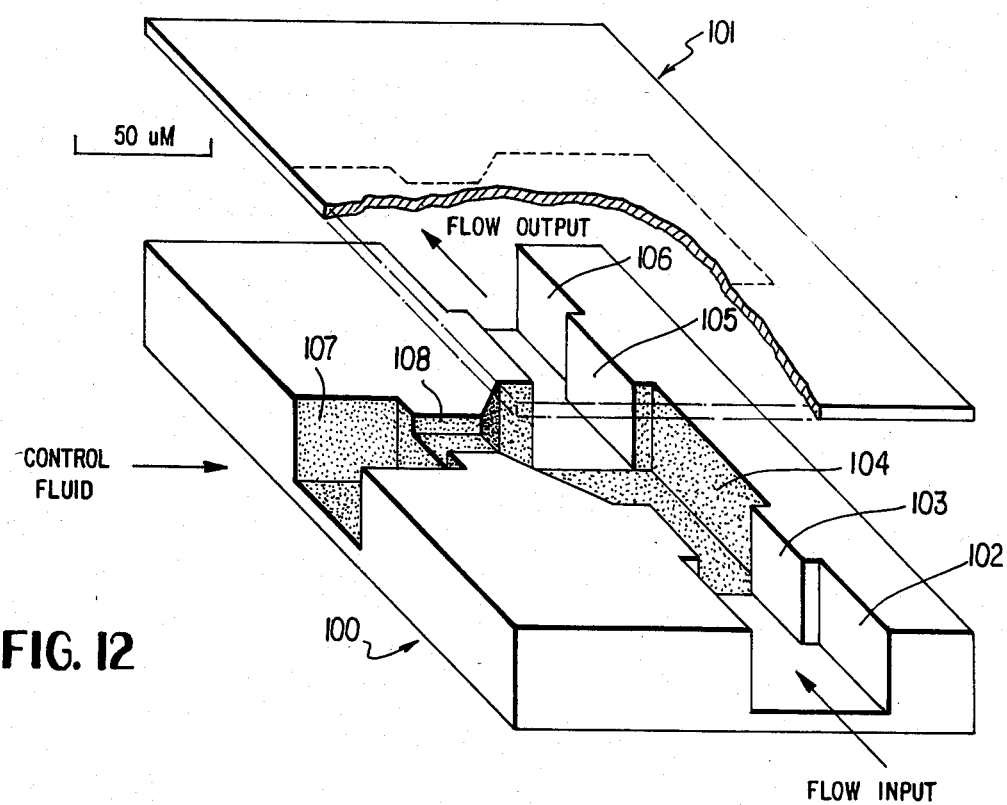
FIG. 12 is an enlarged perspective view illustrating a valve construction suitable for a microsystem.

A practical version of a micro flow control valve according to the present invention is illustrated in FIG. 12. In this Figure, the capillary passages involved are formed by suitable etching or other processes in a glass substrate 100 which is provided with the glass cover plate 101. The substrate 100 with its cover plate 101 may form a microscope slide on which an entire controlled flow system for manipulating cells may be formed, as hereinafter more particularly described.

Thus, the channel 102 formed in the substrate and completed as to its capillary dimensions by the cover plate 101 is precision machined by known techniques and is preferably provided with a necked down portion 103 in its high surface energy level channel 102 before joining the low surface energy level channel 104. It will be appreciated that the restriction provided by the necked down portion 103 (and also at 105) is in conformity with the above discussion regarding the bandwidth feature. The output channel likewise has a necked down portion 105 and a wider channel 106 substantially as is shown. The control fluid channel 107 is likewise necked down as indicated at 108 to merge with the channel 104.

As initially formed, both the substrate 100 and the glass cover plate 101 provide high surface energy glass surfaces for the capillary passages but as is indicated by the stipling in FIG. 12 on the substrate 100, same is treated to provide the low surface energy surface and as is indicated by the dashed line on the cover plate 101, a similar treatment of the underside of the cover plate is provided in conformity with the plan view outline of the lower surface energy surface for the control fluid. For example, this treatment may take the form of the application of Teflon material to the requisite surfaces as indicated.

Another embodiment of this invention utilizing the principles described above is shown in FIGS. 13 and 14. In this embodiment, two control valves in accord with this invention are combined to trap a known volume of principal fluid therebetween. Then, the control valves are again used to expel or pump this known volume of the principal fluid down the capillary line when it is desired to do so.

The material which provides the high surface energy capillary surface is the material indicated generally by the reference character 110 whereas the low surface energy material is indicated generally by the reference characters 111, 112 and 113. The inlet channel 114 defined by the material 110 is necked down as at 115 to provide a stabilizing junction with bandwidth features as previously described and it leads into the volumetric chamber 116 of the chamber section 117 and is thereafter necked down again for bandwidth purposes as indicated by the reference character 118 where it joins the control valve assembly indicated generally by the reference character 119. Donwstream of the control valve assembly 119 is a further section of high surface energy material 110' which is necked down as at 120 opening into the discharge channel section 121, again for bandwitdh purposes. Just downstream of the necked down portion 115 the low surface energy material 112 forms a vent as shown and just upstream of the necked down portion 118 the low surface energy material 113 provides a further vent.

FIG. 13 illustrates the filling stage of this embodiment of the invention. While the principal fluid is filling the pump chamber under the capillary flow of the principal fluid operating in conjunction with the high surface energy material 110, both vents 125 and 126 are open whereas the control valve 119 is closed to prevent the fluid from flowing beyond the assembly. The control valve 119 is closed due to the exogenous gas pressure introduced through the capillary passage 127 and interfaces are formed at the downstream and upstream ends respectively of the necked down portions 118 and 120. The interface at the downstream end of the necked down portion 118 is indicated at 129'. When the volumetric chamber 117 has been completely filled with the principal fluid and the control valve 119 is still closed, it will be appreciated that a known volume of the principal fluid is trapped within the chamber 117. At this time, the pump chamber is completely filled and the interface 130 (shown in FIG. 14 but not in FIG. 13) will also be present which prevents flow of the principal fluid through the capillary 126. At the same time, the principal fluid cannot intrude into the capillaries defining the vents 125 and 126 because of the low surface energy level characteristics of the materials in 111 and 113 and the low surface energy level of the control fluid with respect to the principal fluid.

In order to pump out the volumetric chamber 117, exogenous control fluid pressure is introduced as is indicated in FIG. 14 through the capillary passage 125 while the control valve 119 is opened by venting its capillary passage 127 as indicated. Both of these capillaries 125 and 127 are connected with suitable sources of control fluid having pressure control means associated therewith. It will be noted that in this embodiment, the capillary 126 is always vented to permit proper operation during filling so that it, in effect, is a passive element whose presence is nevertheless essential. The control fluid introduced at 125 forms a stabilized interface 128 at the downstream end of the necked down portion 115 and thereby prevents backflow of the control fluid therebeyond, i.e., a valving action is effected. The interface 130 is already present at the mouth of the capillary 126 where it joins the pump chamber so that as the principal fluid is being expelled from the pump chamber by the travelling interface 129, the only flow path for the principal fluid is through the necked down portion 118. When the travelling interface 129 reaches the downstream end of the necked down portion 118, it is stabilized thereat as is indicated at 129' in FIG. 13.

It will appreciated that the arrangement of FIGS. 13 and 14 allows a predetermined quantity or volume of the principal fluid to be trapped, held and thereafter released for further flow. Two valves are involved, one of which is the main control valve 119 which operates from closed condition in order to permit filling of the pump chamber and to open condition to permit the metered outflow of the trapped principal fluid, and the other of which is the combined valving and expelling action effected by the capillary passage 125.

Figure 15:
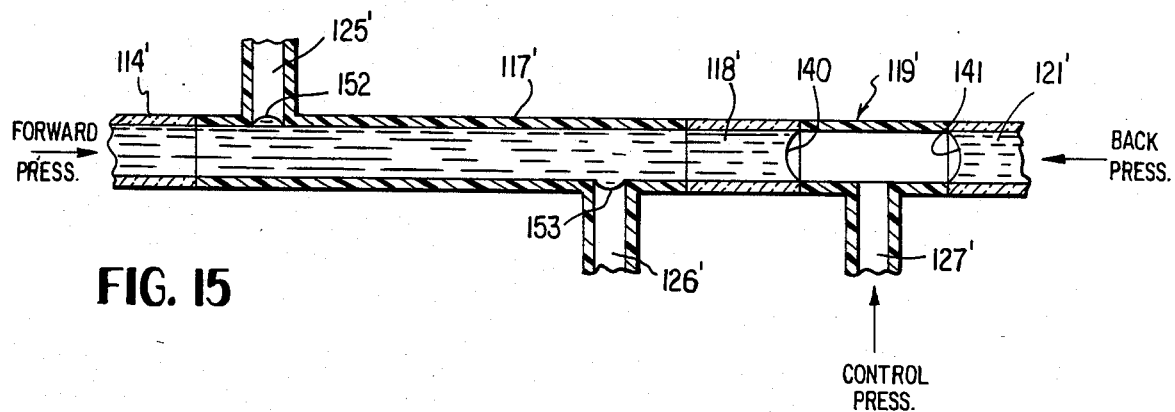
FIGS. 15 and 16 are directed to another embodiment of a metering system.
Figure 16:
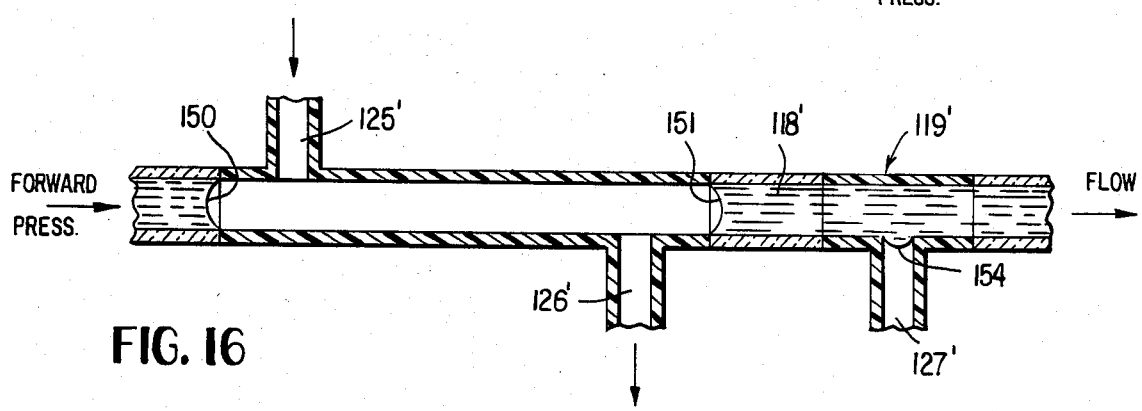

In order to illustrate the principles of FIGS. 13 and 14 on larger scale, reference is had to FIGS. 15 and 16 which are functionally equivalent thereto. Primed reference characters are utilized in FIGS. 15 and 16 to designate generally corresponding portions with respect to FIGS. 13 and 14. FIG. 15 shows the volumetric chamber 117' after complete filling thereof under capillary action, the control fluid being vented both at 125' and 126' at this time so that no exogenous control fluid pressure is functional to prevent this capillary action. The control valve 119' is pressurized through its capillary passage 127' to form the interface 140 and the interface 141 which correspond respectively to the interface 129' in FIG. 13 formed at the downstream end of the necked down portion 118 and the interface at the upstream end of the necked down portion 120. When the capilary passage 127 of the control valve 119' is vented as is shown in FIG. 16, and the capillary passage 125' is subjected to exogenous control fluid pressure while the capillary passage 126' remains vented, the valving interface 150 will form corresponding to the interface 128 in FIG. 14 formed at the downstream end of the necked down portion 115 and, ultimately, the interface 151 is formed which is functionally equivalent to the interface 129' of FIG. 13. Whereas FIG. 13 employs necked down portions to attain the maximum benefits of the bandwidth feature of this invention, FIGS. 15 and 16 do not. Thus, whereas the interface 129' of FIG. 13 is located at the downstream end of the necked down portion 118, the corresponding interface 151 of FIG. 16 is located at the upstream end of the portion 118'. The stabilized interfaces 152, 153 and 154 of FIGS. 15 and 16 are formed and stabilized by virtue of the fact that the material of the relevant capillary passages 125', 126' and 127' are hydrophobic, that is, not wettable by the primary fluid.

Figure 17:
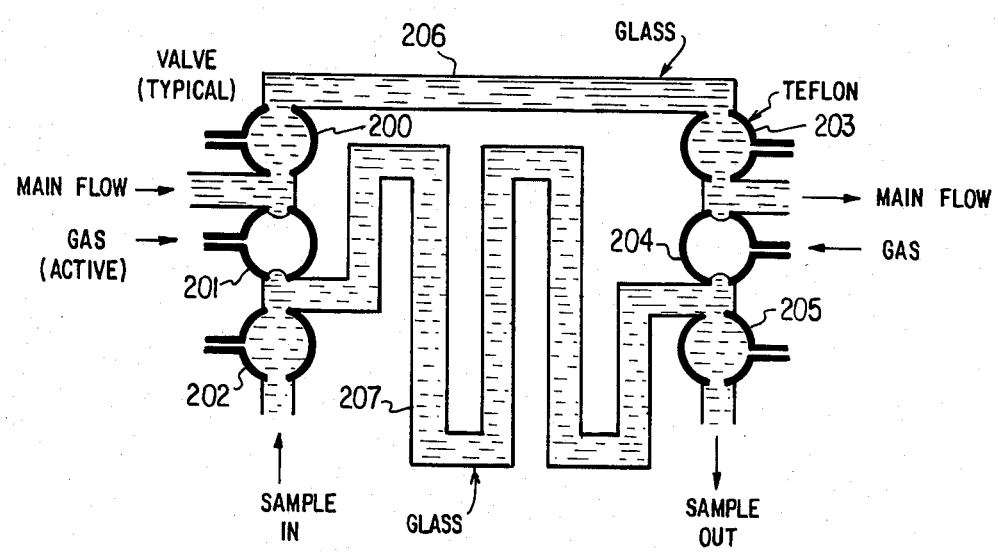
FIG. 17 is a diagrammatic view illustrating the principles of a microsystem according to this invention.

FIG. 17 is a diagrammatic view of a micro flow system which may be made in accord with the principles generally described above in conjunction with FIG. 12 and which may be used in, for example, a cell manipulator system for use while being observed with the aid of a microscope. The system of FIG. 17 employs both the control valves 200 constructed in accord with the FIG. 12 shown and designated respectively by the reference characters 200-205 in conjunction with the capillary section 206 for main flow control and the glass capillary section 207 which, in effect, is a volumetric chamber corresponding to the chamber section 117 of FIG. 13. In the position of the assembly shown in FIG. 17, the valves 201 and 204 are in the active or shut-off state whereas the remainder of the valves 200, 202, 203 and 205 are in the open or inactive state. In this condition, both main flow and sample flow is taking place. If, now, the small volume of sample reagent is desired to be introduced into the main flow, the valves 200, 202, 203 and 205 are made active. This shuts off the sample into the volumetric section 207 and also shuts off the sample output flow. Also, the closing of the valve 200 shuts off the main flow and the closing of the valve 203 shuts off the main flow. If, now, the valve 204 is deactivated, the gas supplied to the valve 202 will pump the entrapped sample in the section 207 through the valve 204 and into the main flow outlet indicated. Similarly, if the valve 203 is deactivated whereas the valve 200 is activated, the predetermined volume of the section 206 of the main flow will be injected into the main flow outlet.

Figure 18:
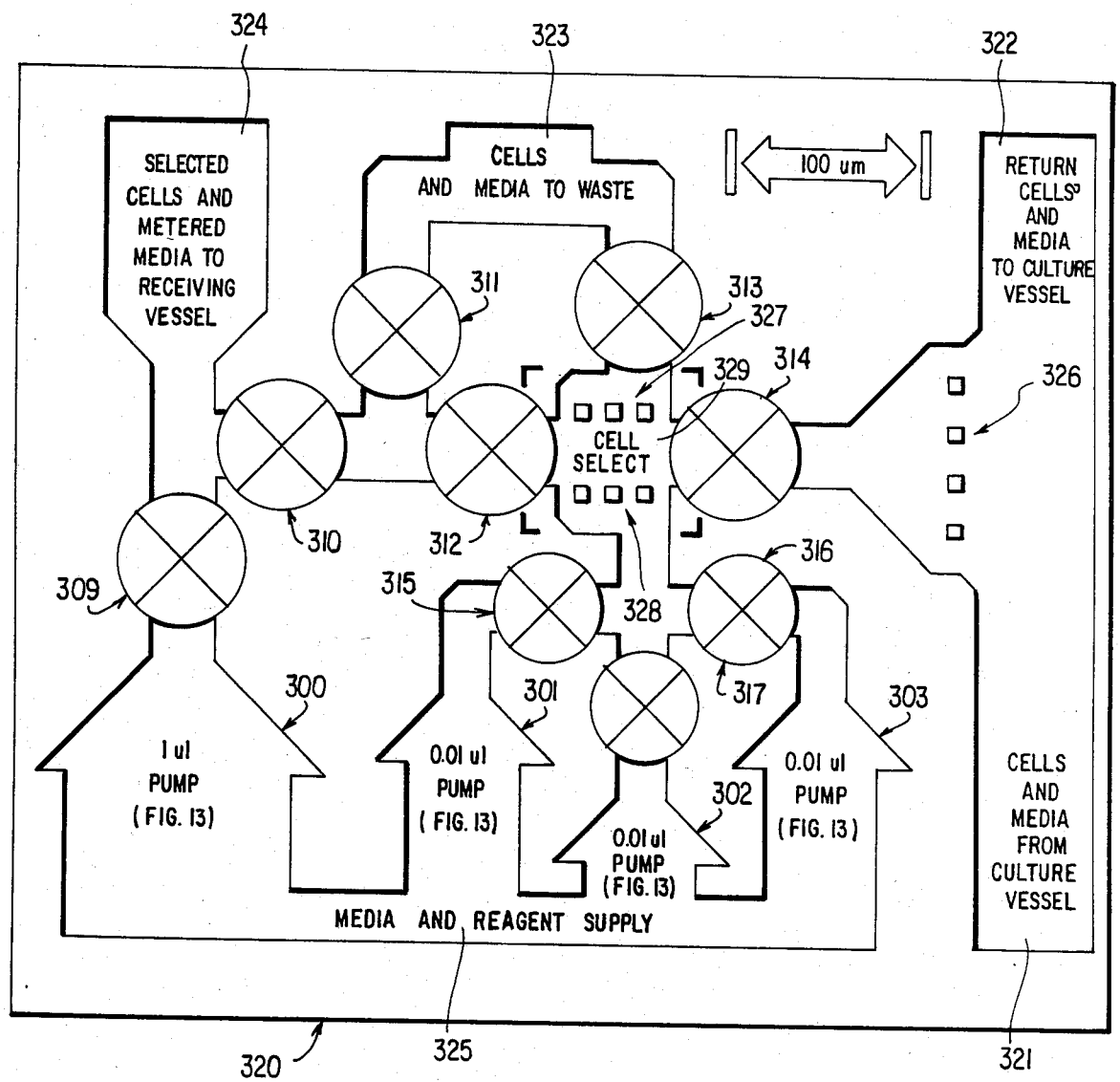
FIG. 18 is a diagrammatic view of another microsystem according to this invention.

As will readily be appreciated from a study of FIG. 17, it is relatively simple utilizing the principles of this invention to manipulate media and reagents in any desired fashion and with respect to this, reference is directed to FIG. 18 wherein a cell manipulator of extremely small size is illustrated. As shown, four pumps indicated generally by the reference characters 300, 301, 302, and 303, all constructed in accord with the principles shown in FIG. 13 are employed. In addition, control valves 309-317 constructed in accord with the principles described in conjunctin with FIG. 12 are also employed. As indicated, the entire assembly is formed on a single substrate indicated by the reference character 320 and a suitable cover plate generally in accord with the principles disclosed in conjunction with FIG. 12.

FIG. 18 has been simplified somewhat for the purpose of clarity. Thus, although the region 321 for cells and media supply is illustrated as being contained within the unit 320, it is to be understood that this supply will in reality be externally supplied. The same is true for the regions 322, 323, 324, and 325. All of these would normally be located separate from the substrate 320 containing the micro flow and manipulator system. In fact, the region 325 shown as a single region would usually be comprised of several regions respectively communicating with the individual pumps 300, 301, 302 and 303.

In addition to the above, the system includes the filters 326, 327 and 328 to aid in the cell selection and manipulation processes. The filter 326 may comprise individual "islands" spaced apart about 30 microns, for initial cell selection. Thus, as that area of the system surrounding the filter 326 is being viewed through a microscope with cells in media passing the filter 326 from region 321 toward region 322, a cell may be tentatively selected by opening the valve 314 to allow such cell and media to flow therethrough and into the cell select region 329. Now the smaller bracketed area may be viewed under increased magnification. The islands of the filters 327 and 328 are spaced apart about 5 microns so that a cell cannot pass therethrough. If the cell is not desired for further study, it may be rejected by opening the valves 311 and 312 and operating one of the pumps 301-333 and flushing it to waste. If the cell is desired for further manipulation, the valves 310 and 311 are opened and one of the pumps 301-313 operated to flush it toward the region 324 whereas the pump 300 ultimately flushes it into the region 324. The reason for the plurality of pumps shown is that once a cell has been selected, a selection of one or more reagents or media to be contacted with it may be desired. Thus, the several pumps should individually be connected to these several supplies rather than to the simplified single supply region 325 as shown.

Figure 19:
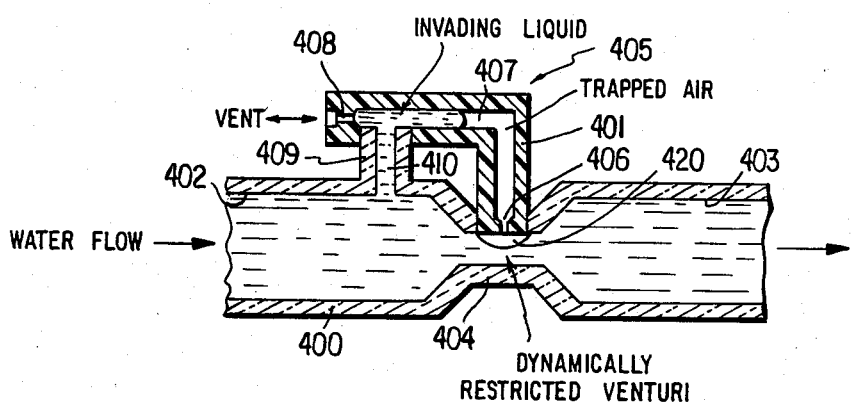
FIG. 19 is a section illustrating a dynamic flow restrictor in accord with this invention.

A further embodiment of the invention is illustrated in FIG. 19 which shows an automatic flow regulator system. The system as illustrated is a water/air system and the material indicated at 400 is of glass whereas that of 401 is of Teflon, although it is to be understood that other and different arrangements in accord with the principles disclosed herein may be employed. The two capillary passages 402 and 403 are joined through the restricted or necked down capillary passage 404 in order to form a venturi effect due to the continuous flow of the water from left to right in FIG. 19. The L-shaped leg 405 formed of Teflon preferably is necked down at 406 where the capillary passage 407 intersects the necked down section 404. The free end of this section 405 is vented, preferably through the necked down portion 408. The glass section 409 defines a capillary passage 410 which intersects the capillary passage 407. Under non-flow conditions, the Teflon side tube 401 of the venturi is filled with air and the glass side tube 409 is filled with water. As water flows through the venturi 404, water rises in the section 409 to intrude within the capillary passage 407 which traps air between it and the necked down portion 406 and causes the air to form a meniscus or interface 420 as shown. This interface restricts the venturi section 404 and regulates the flow through the system, automatically or in a dynamically regulated fashion as dictated by the flow rate of the principal fluid. It will be appreciated that proper configuration of the Teflon tube section 401, i.e., by tapering it, undulating it, etc. will alter the flow/restriction relationship.

What is claimed is:

1. A fluid flow control system for controlling capillary flow of a principal fluid through the intermediary of a control fluid, which comprises;
    capillary passage means for conveying the principal fluid by capillary flow therein and for allowing introduction of the control fluid thereinto;
    means for defining at least two fluid/fluid interface locations within the capillary passage means;
    the principal fluid and the control fluid having different surface energy levels;
    the principal fluid at one of said locations in combination with its contacting portion of said capillary passage means providing a potential energy state which is different from the potential energy state of the control fluid in combination with its contacting portion of said capillary passage means at said one location so that a fluid/fluid interface of one kind between the principal and control fluids may be pressure stabilized at said one location;
    the principal fluid at the other of said locations in combination with its contacting portion of said capillary passage means providing a potential energy state which is different from the potential energy state of the control fluid in combination with its contacting portion of the capillary passage means at said other location so that a fluid/fluid interface of another kind between the principal and control fluids which is opposite said one kind may be pressure stabilized at said other location; and
    control means for causing said control fluid selectively to form a first pressure stablilized fluid/fluid interface of said one kind between the principal and control fluids at said one location and selectively to form a second pressure stabilized fluid/fluid interface of said another kind between the principal and control fluids at said other location so as to control capillary flow of the principal fluid through said capillary passage means.

2. A fluid flow control system as defined in claim 1 wherein said means defines a third fluid/fluid interface location.

3. A fluid flow control system as defined in claim 2 wherein said control means forms pressure stabilized fluid/fluid interfaces between the principal and control fluids at two of said locations so as completely to block said capillary passage means and thereby provide a valving action.

4. A fluid flow control system as defined in claim 3 wherein said means defines a fourth fluid/fluid interface location.

5. A fluid flow control system as defined in claim 4 wherein said control means provides closed valving actions at two of said locations which are longitudinally spaced within said capillary passage means and a venting action at another location between said two locations.

6. A fluid flow control system as defined in claim 3 wherein said control means provides closed valving actions at two of said locations which are longitudinally spaced within said capillary passage means and a venting action at another location between said two locations.

7. A fluid flow control system as defined in claim 1 wherein said fluid/fluid interface locations are closely adjacent each other.

8. A fluid flow control system as defined in claim 7 wherein the areas of said locations are dissimilar.

9. A fluid flow control system for controlling capillary flow of a principal fluid through the intermediary of a control fluid, which comprises:
    capillary passage means having a first path for conveying the principal fluid by capillary flow therein and a second path for allowing introduction of the control fluid into said first path;
    means for defining at least one fluid/fluid interface location within said first path and a second fluid/fluid interface location at the junction of said second path with said first path;
    the principal fluid and the control fluid having different surface energy levels;
    the principal fluid at said one of said locations in combination with its contacting portion of said capillary passage means providing a potential energy state which is different from the potential energy state of the control fluid in combination with its contacting portin of said capillary passage means at said one location so that a fluid/fluid interface of one kind between the principal and control fluids may be pressure stabilized at said one location;
    the principal fluid at said second location in combination with its contacting portion of said capillary passage means providing a potential energy state which is different from the potential energy state of the control fluid in combination with its contacting portion of the capillary passage means at said second location so that a fluid/fluid interface of another kind between the principal and control fluids which is opposite said one kind may be pressure stabilized at said second location; and
    pressure control means for exerting a first pressure on said control fluid to form a first pressure stabilized fluid/fluid interface of said one kind between the principal and control fluids at said one location and for exerting a second pressure on the control fluid to form a second pressure stabilized fluid/fluid interface of said another kind between the principal and control fluids at said second location so as to control capillary flow of the principal fluid through said capillary passage means.

10. A fluid flow control system for controlling capillary flow of a principal fluid through the intermediary of pressure control to a control fluid, which comprises:
first capillary passage means for conveying the principal fluid by capillary flow therein and for defining at least first and second junctions within said capillary passage means at which pressure stabilized fluid/fluid interfaces may be formed between the principal and control fluids;
second capillary passage means intersecting said first capillary passage means between said first and second junctions for conveying the control fluid and for defining a third junction at which a pressure stabilized fluid/fluid interface may be formed between the principal and control fluids;
the principal fluid and said control fluid having different surface energy levels;
the principal fluid at the first and second junctions in combination with the portions of the first capillary passage means with which it is then in contact having a potential energy state of a sense different from the potential energy state of the control fluid in combination with those portions of said first capillary passage means with which it is then in contact so that the fluid/fluid interfaces at said first and second junctions may be pressure stabilized;
said principal fluid at the third junction in combination with that portion of said second capillary passage means with which it is then in contact having a potential energy state opposite to said sense from the potential energy state of the control fluid in combination with that portion of the second capillary passage means with which it is then in contact so that the fluid/fluid interface at said third junction may be pressure stabilized; and
pressure control means connected with said second capillary passage means for selectively exerting a first control pressure on said control fluid which forms a pressure stabilized fluid/fluid interface between the principal and control fluids at said third junction without causing the control fluid to fill said first capillary passage means and block capillary flow of the principal fluid therethrough and a second control pressure on the control fluid which causes the control fluid to fill said first capillary passage means between said first and second junctions and form stable fluid/fluid interfaces between the principal and control fluids at said first and second junctions so as to block capillary flow of the principal fluid through said first capillary passage means.

11. A capillary flow metering system suitable for controlling the flow of a principal fluid through the medium of a control fluid comprising the combination of:
flow passage means for conveying the principal fluid and defining a pair of spaced junctions;
each junction being formed between a first capillary surface and a second capillary surface having different surface energy levels and the principal fluid in combination with the first and second capillary surfaces providing different potential energy states which are respectively different from the potential energy states of the combination of said control fluid with said first and second capillary surfaces;
said junctions defining an upstream junction and a downstream junction within said flow passage means;
inlet capillary passage means defining an inlet capillary surface having a different surface energy level than said first surface for resisting flow of said principal fluid into the inlet capillary passage means while allowing the control fluid to be introduced into the space between said junctions;
pressure control means for selectively controlling the pressure in the control fluid in said inlet capillary passage means between one pressure allowing flow of the principal fluid through the flow passage means and a higher pressure introducing the control fluid into said space to form fluid/fluid interfaces at the upstream and downstream junctions which block the flow of said principal fluid through said flow passage means; and
valve means adjacent said downstream junction for permitting a predetermined volume of principal fluid to fill between said junctions.

* * * * *